United States Patent [19]

Parrish

[11] 4,448,207

[45] May 15, 1984

[54] MEDICAL FLUID MEASURING SYSTEM

[75] Inventor: John H. Parrish, La Jolla, Calif.

[73] Assignee: Vital Metrics, Inc., San Diego, Calif.

[21] Appl. No.: 317,611

[22] Filed: Nov. 3, 1981

[51] Int. Cl.³ .......................... A61B 5/00; G01F 23/28
[52] U.S. Cl. ............................... 128/771; 73/290 V; 73/861; 604/318; 604/322
[58] Field of Search ................. 73/290 V, 223, 861, 73/293, 296; 128/768, 771; 604/322, 317, 318, 260; 367/908

[56] References Cited

U.S. PATENT DOCUMENTS

| | | | |
|---|---|---|---|
| 4,130,018 | 12/1978 | Adams et al. | 73/290 V |
| 4,210,969 | 7/1980 | Massa | 73/290 V |
| 4,219,177 | 8/1980 | O'Day | 604/322 |
| 4,229,798 | 10/1980 | Rosie et al. | 73/290 V |
| 4,305,405 | 12/1981 | Meisch | 128/768 |
| 4,343,316 | 8/1982 | Jespersen | 128/771 |

OTHER PUBLICATIONS

Kharitonov et al., "Device for measuring the urine flow rate", *Biomed. Eng.*, V. 11, No. 2 (Mar.-Apr. 1976), pp. 104-106.
Condon, "Measurement of hourly urine output in a closed system", *Surgery*, V. 56, No. 2 (Aug. 1964), pp. 378-379.

*Primary Examiner*—Gerald Goldberg
*Assistant Examiner*—John E. Chapman, Jr.
*Attorney, Agent, or Firm*—Freilich, Hornbaker, Rosen & Fernandez

[57] ABSTRACT

A urine discharge measuring system for medical use which includes a gimbal mounted frame supporting a urine container of fixed dimensions to collect urine from a urinary catheter attached to a patient. An ultrasonic transceiver mounted above the container and operated in conjunction with a microprocessor based control unit, positioned adjacent to the transceiver, periodically and automatically measures the height of the urine collected within the container. The measured fluid height is converted to fluid volume by the control unit. To maintain the sterility of the container, the transceiver transducer(s) is mechanically isolated from the urine container by elements which allow the ultrasonic energy to be transmitted to and received from the interior of the container. In one described embodiment, desired measured volume accuracy is achieved by employing a reflective target within the urine container at a known fixed distance from the transceiver transducer. Comparison by the control unit of the measured distance with the actual distance to the target allows generation of corrections for variations of the speed of sound in air due to temperature and humidity to be applied when obtaining the urine height within the container. Digital displays in the control unit provide indication of past and present accumulation of the urinary output of the patient.

18 Claims, 11 Drawing Figures

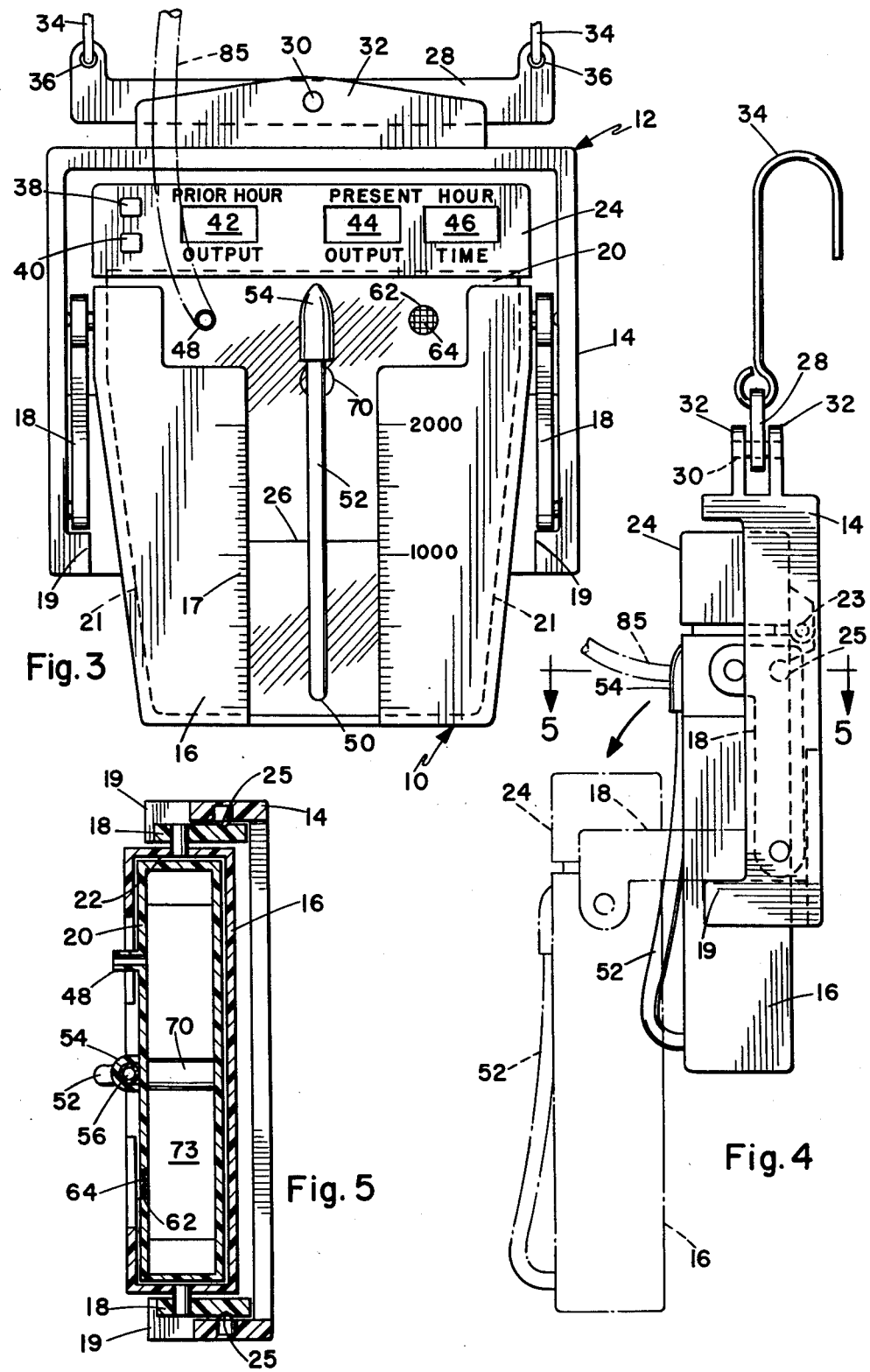

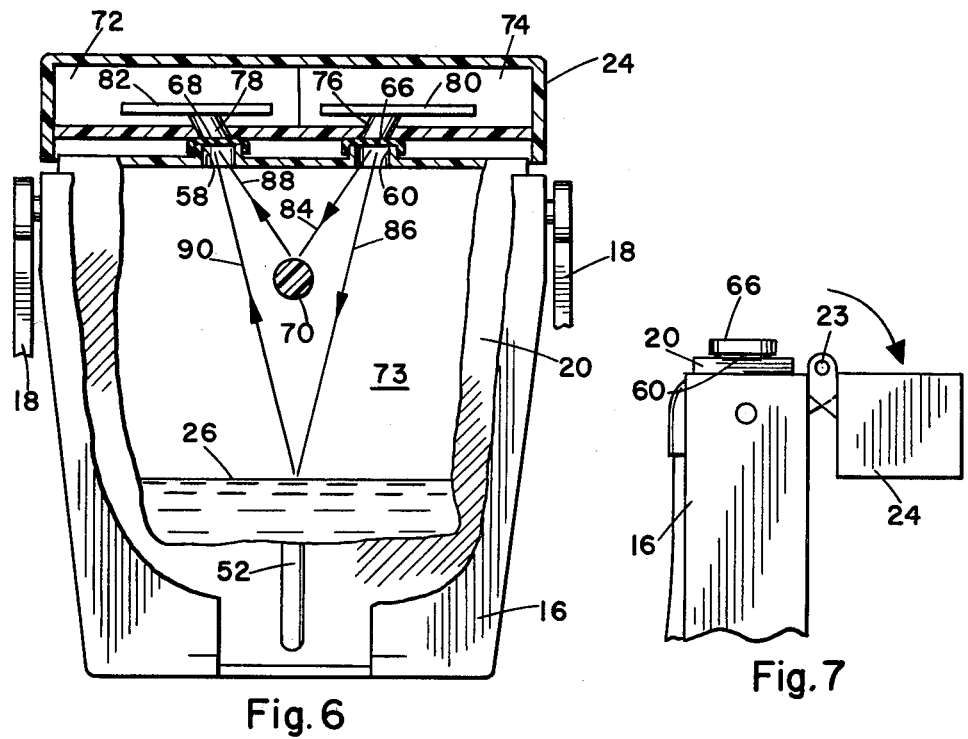
Fig. 6
Fig. 7
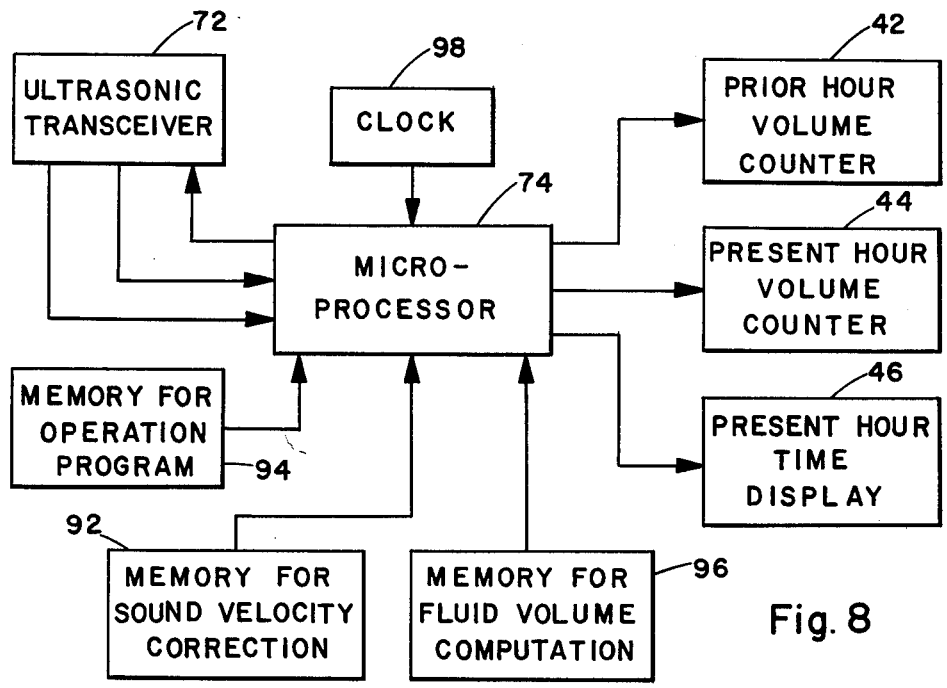
Fig. 8

MEDICAL FLUID MEASURING SYSTEM

BACKGROUND OF THE INVENTION

Obtaining accurate and consistent intake and output measurements of fluids is a matter of very high priority in treating critically ill hospital patients. Intake measurements are essential to insure that the prescribed volume and rate of parenteral/interal solutions are delivered so that the desired therapeutic effect occurs. Accurate and consistent output measurements are essential to insure that fluid overload as a result of over infusion, depressed cardiac output, or post-renal failure have not occurred. Acute changes in urine flow can be the earliest evidence, even before changes in the vital signs of blood pressure, temperature, pulse, or respiration of a deteriorating clinical condition in the patient.

For a critically ill patient who does not have primary renal failure, the flow and volume of urine produced by the kidney is dependent upon adequacy of renal blood flow. Since cardiac output is the primary determinant of renal flow, changes in urine output are correlated with changes in cardiac output. Thus, an accurate measurement of the rate of urine flow and volume can supply a physician with information relating to potential circulatory arrest and acute renal failure. A brief episode of only five minutes of hyper-tension to 66 percent of the patient's normal blood pressure may be sufficient to cause an episode of acute renal failure.

In addition, renal system response to intravenous fluid or blood infusion as observed by change in volume of urinary output, can supply a physician with information about the pathological process responsible for low urinary output. The most common etiology of low urinary output is depressed cardiac output caused by too much fluid volume, but other causes include: primary renal failure, heart failure, or post-renal obstruction.

For the critically ill patient, changes in hemodynamic measurements of cardiac output such as arterial blood pressure, central venous pressure, and left atrial pressure are meaningless if these changes are not correlated with changes in the perfusion of major organs such as the kidney. A urine measuring and display system that can supply the physician indirect information about renal perfusion in the form of changes in the urine volume will insure that he has available the necessary physiologic data to make sound clinical decisions.

Available catheterized patient output volume measuring and collection devices are of three principal designs. Older units are flexible bags or semi-rigid clear plastic disposable collection containers with graduations in 25 or 50 milliliter increments up to 2,000 milliliters. A second system typically consists of a 2,000 milliliter clear flexible bag that incorporates a rigid clear plastic 200 milliliter reservoir which is graduated, initially, in 2 milliliter increments. In these latter instruments, urine flows down a drainage tube into the rigid reservoir. Either every 30 minutes, or hourly, a staff member must measure and record the urine output and then empty the urine from the smaller rigid reservoir into the larger flexible bag, so that the measuring cycle can begin again. Such devices lack accuracy, and are dependent upon precise time interval measurement and recording to establish an accurate record of output. They are difficult to read because the containers hang below the bed. Also, additional time is consumed because of having to transfer the urine from the rigid reservoir into the larger container to begin the measurement cycle again.

A third type of urinary drainage monitor electromechanically separates urine output hourly into one of ten compartments in a disposable unit. This system eliminates emptying of urine from a urinary reservoir every 30 minutes of hourly, but it also lacks accuracy. Its graduations are hard to read, and the design makes it difficult to take thirty minute interval output measurements, resulting in the likelihood that nurses might not check the output every eight hours or at a shift change. The unit is also expensive.

The present invention overcomes the disadvantages set forth for previous systems by employing a system composed of a reusable electronic unit which measures urine output volume to within plus or minus 2 milliliter accuracy using ultrasonic technology. It has digital displays of urine output and time for both the present hour and the prior hour.

SUMMARY OF THE INVENTION

According to the invention, a medical fluid measuring system has been devised wherein urine outflow from a catheterized patient can be automatically and accurately measured and displayed. According to the precepts of the invention urine is collected in a clear disposable rigid container wherein it can be viewed, yet is isolated to prevent contamination.

In the exemplary embodimets, the system comprises three principal components. A support assembly houses a removable and disposable container with known fixed dimensions within which the urine from a catheterized patient is collected. Mounted atop the support assembly is a measuring and control unit including an ultrasonic measuring transceiver, a microprocessor, and displays, all of which are bacteriologically isolated from the urine collected in the disposable container. The microprocessor controls the timing and operation of the transceiver to periodically determine the height of the urine accumulated in the collecting container by echo sounding to the surface of the collected urine. Based upon these measurements and the known dimensions of the container, the microprocessor calculates the volume of fluid accumulated with time, and causes this information to be displayed for the current and preceding hour. To assure accuracy, the support assembly has gimbaled mountings to permit the surface of the collected fluid to remain level with variations in the unit mounting. In one embodiment, wherein the height of the accumulated liquid is determined by echo sounding through a significant air space, a target within the urine container having a known distance from the transceiver transducers is used in conjunction with the microprocessor to permit correction of the measured distance to the fluid level for variations in air temperature and humidity within the container. In a second embodiment the height of the accumulated liquid is determined by echo sounding through the depth of the accumulated liquid, and the target is not required.

It is an object of the invention to provide a new and improved medical fluid measuring system. The system automatically and accurately determines the volume of fluid with time in an isolated urine container. The system is convenient to use and its displays are easily observed in presenting summaries for the present and preceding hour by digital indication for easy tracking of a patient's renal system functioning. The system is automatic in operation and does not require draining for continuing measurement which results in assured measurement and the saving of valuable staff time. Collected urine may be easily observed in, and samples taken from the system for further analysis. The system is relatively inexpensive.

Other objects and many attendant advantages of the invention will become more apparent upon reading the following detailed description together with the drawings, in which like reference numerals refer to like parts throughout, and in which:

FIG. 3 is a front view of the apparatus.

FIG. 4 is a side elevation view of the apparatus showing the holder swung out for replacement of the urine container.

FIG. 5 is a sectional view taken on line 5—5 of FIG. 4.

FIG. 6 is a front view of the holder and urine container with portions cut away to show the ultrasonic measurement operation.

FIG. 7 is a side elevation view of the holder with the top hinged open for access to the urine container.

FIG. 8 is a functional block diagram of the measurement and control unit of the system.

DETAILED DESCRIPTION OF THE DRAWINGS

Figure 1:
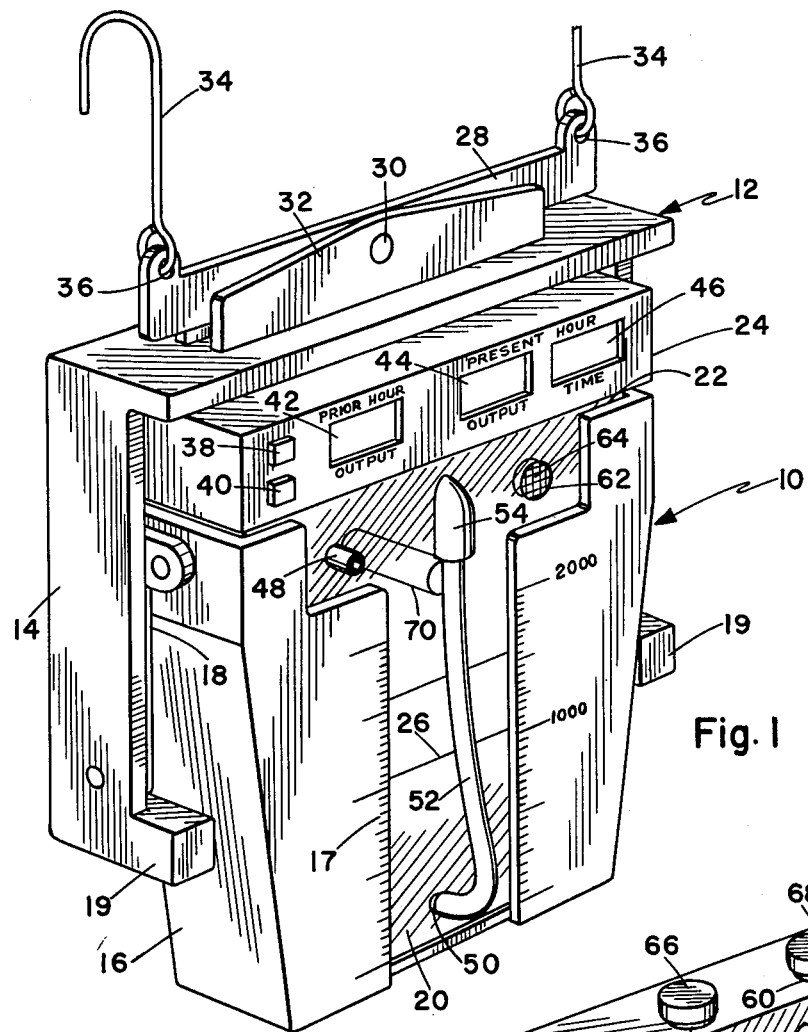
FIG. 1 is a perspective view of the fluid measuring apparatus.

Referring to FIG. 1, the illustrated embodiment of the body fluid measuring system 10 of the present invention is shown to include a support assembly 12 which is mountable upon the bed of the patient, or at a convenient adjacent location. Support assembly 12 consists of a mounting frame 14 and a fluid container holder 16 that is pivotally connected by rotating arms 18 to the mounting frame 14 so that the holder may be lowered from the frame 14 to a position where arms 18 rest upon stops 19 of the frame in order to permit insertion and removal of container 20 from a container recess 22 formed in the holder 16. The container holder 16 is illustrated in its lowered position in FIG. 4. A graduated scale on the face of holder 16 calibrated with 50 milliliter marking permits visual determination of urine volume within container 20.

As further illustrated in FIGS. 4 and 7, the control and measuring unit 24 is hingedly mounted by hinge 23 at the top of container holder 16 so as to be spaced operationally adjacent to the top of container 20, or rotated clear of recess 22 for changing the container 20. Detents 25 secure the holder 16 to mounting frame 14 when the fluid measuring system 10 is in its up or measuring configuration.

As illustrated in FIGS. 3 and 4, the design of mounting frame 14 permits gimbal mounting of the fluid measuring system 10 so as to maintain the surface 26 of the fluid collected in container 20 level. This is achieved by pivotally mounting attachment arm 28 at the center of mounting frame 14 with a pivot pin 30 which in turn is supported between the mounting ears 32. The attachment arm 28 is secured by means of support hooks 34 connected in apertures 36 of the attachment arm 28 and to the desired location for measuring system 10. By this design, measuring system 10 may rotate sufficiently about its vertical and horizontal axes to permit the fluid surface 26 to remain horizontal for accurate measurement of the surface height.

The control switches and displays of the control and measurement unit 24 are illustrated in FIG. 1, and are manipulated and viewed at the face of the fluid measuring system 10. Power switch 38 controls the electrical power for the operation of unit 24, while switch 40 resets the displays. Digital display counter 42 presents the total volume of fluid accumulated in the container 20 within the prior hour of operation of measuring system 10. Digital display 44 indicates the accumulated fluid in the container 20 for the present hour and is used in conjunction with display 46 which indicates the elapsed time in the present hour of measurement.

Figure 2:
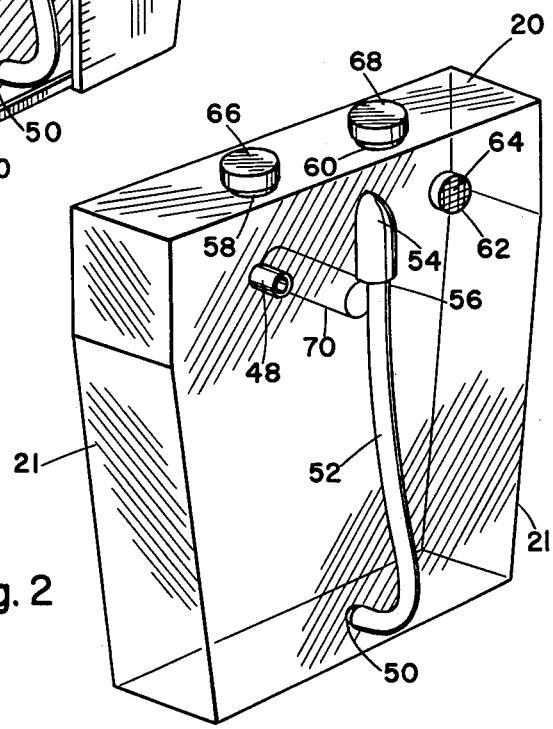
FIG. 2 is a perspective view of the disposable urine container.

The details of construction of container 20 are depicted in FIGS. 2 and 5. The container of the embodiment has a 2000 milliliter fluid capacity and is of rigid construction formed of a clear plastic so that the fluid contents of the container can be visually observed. The container 20 is molded to have fixed interior dimensions to permit accurate calculation of contained fluid volume as will be subsequently described. The container 20 has tapered side sections 21 to facilitate its entry and removal from recess 22 in container holder 16 (FIG. 2). Container 20 is provided with a catheter input tube connection 48 near its top, and a container drain connection 50. A section of flexible tubing 52 is permanently connected to drain connection 50. Drain tube holder 54 is a fitting on the front of container 20 designed to secure the free end 56 of the tube section 52. A bend in tube section 52 closes the drain connection 50. The container 20 is designed as a disposable element of the fluid measuring system 10. Therefore, the drain arrangement described is not essential to the measuring function of the system, but is provided so that samples of the collected urine may be subsequently taken for further examination. A container vent opening 62 is provided near the top of container 20 to prevent the build up of pressure within the container as it is filled by the urine input from the catheter. The vent opening 62 is guarded by bacterial filter 64 to prevent contamination of the collected urine by bacteria in the outside air. Collar shaped caps 58 and 60 located on the top of container 20 serve to provide an interface with the other components of the measuring system 10 which are contained within the control and measuring unit 24. Flexible diaphragms 66 and 68 seal the openings of the caps 58 and 60 respectively, bacteriologically isolating the contents of container 20 from the rest of the system.

As illustrated in FIGS. 2 and 5, the container 20 is provided with a target bar 70 located in its interior and positioned at a known distance from the membranes 66 and 68. Target bar 70 provides a known reference distance for computation of measured fluid height corrections resulting from variations of temperature and humidity within the container 20 during system operation. The measuring system 10 of the embodiment is provided with means for correction of sound velocity in order to maintain 2 milliliter accuracy in fluid volume measurement.

As illustrated in FIGS. 6 and 8, the control and measuring unit 24 contains an ultrasonic transceiver section 72 and a microprocessor section 74, in addition to the control switches and displays previously mentioned. In this embodiment, the ultrasonic transceiver 72 (including its send transducer 76 and its receive transducer 78) will be assumed to operate at a frequency of 200 KHz. It should be recognized, however, that other suitable operating frequencies could be employed. The transducers 76, 78 are preferably of the ceramic bender type constructed of a piezoelectric element bonded to an aluminum plate. The transducers 76 and 78 are mounted on support elements 80 and 82 such that the faces of the transducers bear against the center of the diaphragms 66 and 68 that cover caps 58 and 60 respectively of container 20. Because of the compatibility of the diaphragms with the sound to be sent and received, sound pulses generated within the transceiver section 72 are transmitted to the air medium within the interior 73 of container 20. As depicted in FIG. 6, the transmitted pulses 84 and 86 are reflected from both the fluid surface 26 and the target bar 70 within the container 20 for subsequent reception by the receive transducer 78 and further processing within the transceiver section 72 and microprocessor section 74. This embodiment employs both a send and receive transducer, but it should be recognized that a single transducer could fulfill the function with appropriate multiplex circuitry.

Figures 9, 10:
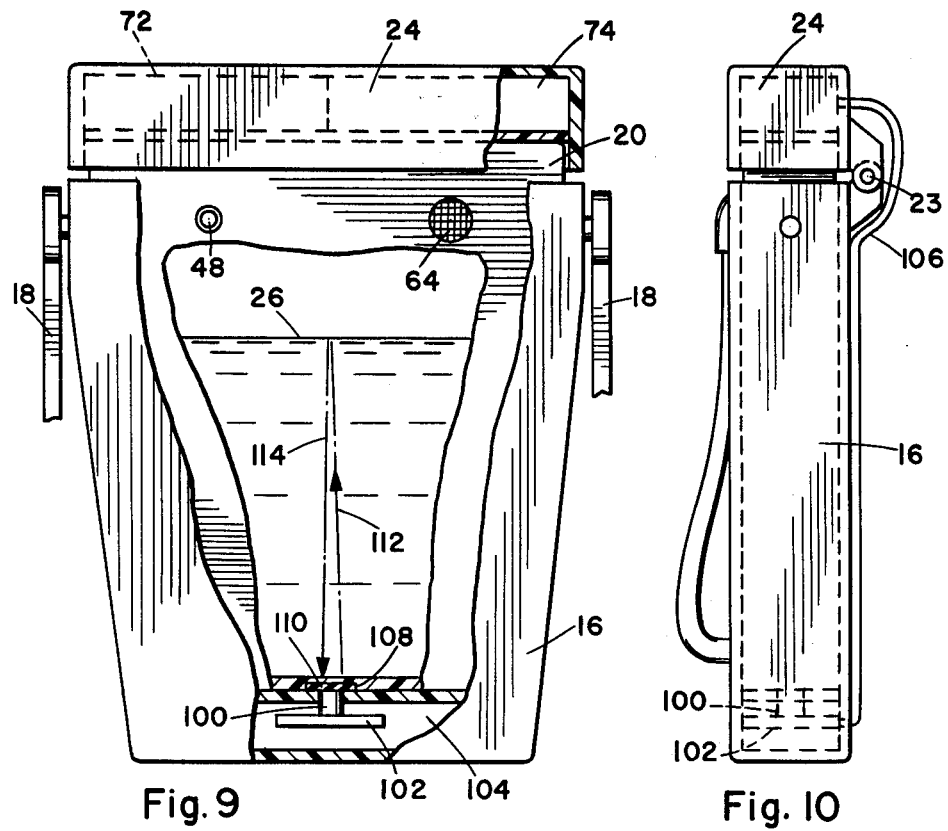
FIG. 9 is a view similar to FIG. 6, showing an alternative ultrasonic transducer arrangement.
FIG. 10 is a side elevation view of the structure of FIG. 9.
Figure 11:
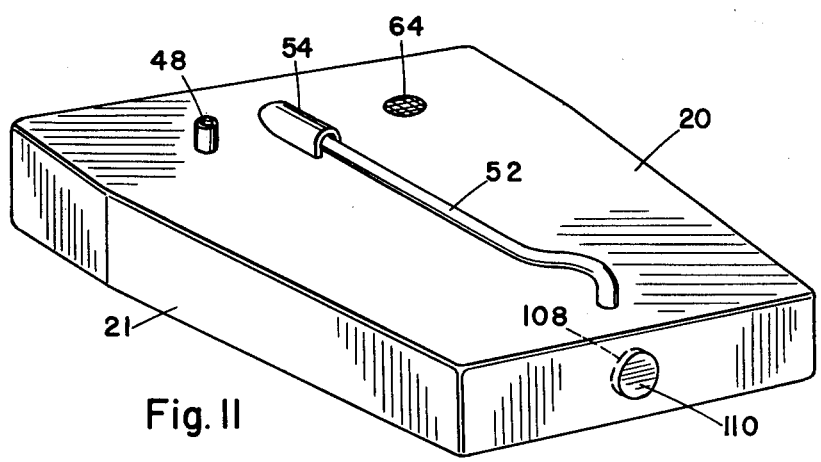
FIG. 11 is a perspective view of the disposable container for use with the unit of FIGS. 9 and 10.

An alternate embodiment of the medical fluid measuring system is illustrated in FIGS. 9, 10, and 11. In this second embodiment, advantage is taken of the ability to measure the height of the urine accumulated by echo sounding through the collected urine to the air urine interface 26 within container 20. To achieve this result, a single send and receive transducer 100 is bacteriologically isolated from the contents of container 20, being installed on a support bar 102 in a compartment 104 located in the base of the container holder 16. Electrical connection from the transceiver section 72 to the transducer 100 is made by leads 106 which are routed along the exterior of the container holder 16. The disposable container 20 of the second embodiment performs the same functions, and is supported within the support assembly 12 as has been previously described. In this embodiment, however, container 20 has a centered recess 108 in its base into which is fitted a disc shaped insert 110 which provides an interface between transducer 100 and the plastic of the container 20 to facilitate transmission of the sound energy to and from the transducer 100 to the liquid within the container. Insert 110 is made from silicone rubber having a minimum hardness of approximately 30 durometers.

In the embodiment illustrated in FIG. 9, a sound pulse 112 is transmitted upwardly from transducer 100 to the surface 26 of the accumulated fluid within container 20. Transducer 100 also receives the return echo 114. Because of the minimal air transmission paths of pulse 112 and 114 involved in this second embodiment, means for air temperature and humidity correction is not necessary, and therefore the target 70 and other correction features of the first described embodiment are not used. The liquid transmission path of the pulses and accuracy requirements for this second embodiment necessitate the selection of a higher operating frequency for the transceiver 72 and transducer 100. A frequency in the range of 5 megahertz is employed.

OPERATION

The overall operation of the system of FIG. 1 may now be described in conjunction with FIGS. 6 and 8. FIG. 8 is a functional block diagram of the control and measurement unit 24. Assume that the body fluid measuring system 10 is mounted near a patient and in its operational configuration, and that a catheter tube connection 85 (FIG. 4) has been made to the container 20 at input connection 48. The system is started by operation of the power switch 38 and the counter displays set to 0 using switch 40. The clock 98 inputs elapsed time to the microprocessor 74 for control of the ultrasonic transceiver 72 and displays 42 and 46. At intervals of four seconds in the described embodiment, the microprocessor sends a pulse of 100 microsecond duration to the transceiver 72. It is recognized, however, that other suitable pulse rates and durations could be utilized. The transceiver converts the pulse to a sonic signal that is transmitted by transducer 76 through diaphragm 66 to the interior of container 20. The transmitted pulse of sound energy represented by lines 84 and 86 in FIG. 6 are reflected by target bar 70 and surface 26 of the accumulated urine received from the catheter drain. The sonic echoes, represented by lines 88 and 90, are received by the receive transducer 78 through diaphragm 68, and are processed by the transceiver 72 and delivered to the microprocessor 74 where the height of the fluid is determined by the time difference between the transmitted pulse and the respective echos received from the liquid surface 26 and target 70. A comparison, managed by the operational program 94, between the measured echo return time to the target 70 against information stored in memory 92, provides sound velocity corrections for correction of the measured urine surface height due to temperature and humidity conditions existing within the collector 20. To improve the reliability and accuracy of the fluid height measurement, an electronic receive window, managed by the microprocessor operational program, and coordinated with the initiation of the transmitted pulse is used to eliminate processing of false echos.

Based upon the known interior dimensions of urine container 20, memory 96 contains tabular fluid volumes based upon the measured height of fluid within the container. Utilizing the operational program 94, the clock 98 and memory 96, the microprocessor determines the volume of urine accumulated in the container 20 with time and displays the volume amount and time on digital counter displays 44 and 46. After an hour's operation, the prior hour urine accumulation is displayed on counter 42, and present hour urine volume and time are displayed on counters 44 and 46.

Operation of the medical fluid measuring system utilizing the second embodiment is essentially the same as has been described. With the latter configuration, however, the height to the fluid level 26 in the container 20 is measured directly and transmitted to the microprocessor 74 for calculation of the liquid volume employing the operational program 94 and memory 96. The operational program 94 is modified to eliminate the correctional computations for sound velocity in air previously described and memory 96 is not used.

When it is necessary to remove or replace the urine container 20, the system is turned off using power and reset switches 38 and 40 respectively. As illustrated in FIGS. 4 and 7, the container holder 16 is unlatched by depressing detents 25, and lowered by rotation of arms 18. The control and measurement unit 24 is then rotated clear about hinge 23. The used urine container 20 may then be removed and replaced from recess 22 in holder 16. With a new container in place, the measuring system 10 is restored to its operational condition by raising and latching the container holder 16 and restarting the system.

Having described my invention, I claim:

1. A medical system for measuring liquids discharged from a patient's body comprising:
   housing means,
   a substantially rigid wall container removably mounted in the housing means for collecting liquid discharged from said patient's body,
   ultrasonic measuring means mounted in the housing means in operational relationship to the container and bacteriologically isolated from the interior of the container for measuring the distance to the surface of the liquid collected within the container,
   control means for determining the volume of liquid collected in the container in a defined time interval in response to the output of the measuring means,
   display means for visually indicating the volume of liquid collected in the container in a defined time interval as determined by the control means, and
   means for connecting the container to said patient's body to collect therein liquid discharged from said body.

2. A medical system according to claim 1, including:
   a vent opening in the container including a bacterial filter to prevent contamination of the liquid collected within the container by bacteria in the outside air.

3. A medical system according to claim 1 wherein:
   the control means includes a microprocessor.

4. A medical system according to claim 3, wherein the control means further includes:
   clock means for providing time information,
   memory means for storing an operational program, and
   processor means coupled to the memory means, ultrasonic measuring means, display means, and clock means for periodically deriving the distance to the liquid level in the container and determining and displaying the volume of the liquid within the container.

5. A medical system according to claim 1 including gimbal means for maintaining said container in a level orientation.

6. A medical system according to claim 1, wherein:
   the display means automatically indicates the volume of liquid collected in the container for the past hour and present hour of system use.

7. A medical system according to claim 1 further comprising:
   means for correcting the output of the measuring means for variations in temperature and humidity within the container.

8. A medical system according to claim 7, wherein the correction means includes:
   a sonic target located within the container at a known distance from the ultrasonic measuring means,
   comparing means for deriving corrections to the measured fluid height based on variations between the actual and measured distance to the target means.

9. A medical system according to claim 1 wherein:
   the ultrasonic measuring means is physically separated from the interior of the container by a thin flexible diaphragm.

10. A medical system according to claim 1, wherein:
    the ultrasonic measuring means includes a resilient coupling element to facilitate sound transmission.

11. A method of determining the volume of liquid discharged from a patient's body in a defined time interval, comprising the steps of:
    connecting a container of known interior dimensions to a patient's body, said container being removably mounted in a housing, accumulating said discharged liquid in said container,
    periodically measuring the height of the accumulated liquid in the container by use of an ultrasonic transducer mounted in said housing and bacteriologically isolated from the liquid in said container
    periodically deriving the volume of accumulated liquid in the container based upon the measured height of the liquid,
    continually measuring elapsed time; and
    visually displaying the derived volume of the liquid accumulated within the container within a measured elapsed time interval.

12. The method of determining the volume of liquid according to claim 11, wherein said step of measuring the height of the liquid level includes the further step of correcting for variations in temperature and humidity existing within the container.

13. Medical apparatus for measuring the discharge of liquids, such as urine, from a patient's body comprising:
    a substantially rigid wall container having top and bottom portions and including an inlet port in said top portion;
    a flexible tube having a distal end coupled to said container inlet port and a proximal end adapted to be coupled to said patient's body for accumulating liquid discharged from said body in said container;
    housing means for removably receiving said container to orient said container with said top portion vertically above said bottom portion;
    measuring means in said housing means including transducer means bacteriologically isolated from the liquid in said container for measuring the quantity of said liquid in said container and clock means for measuring elapsed time; and
    means responsive to said measuring means for displaying the quantity of liquid accumulated in said container within a defined time interval.

14. The apparatus of claim 13 wherein said measuring means includes first means for representing the quantity of liquid in said container and second means for representing elapsed time;
    means actuatable to reset said second means for initiating a present interval; and wherein
    said means for displaying is responsive to said first and second means for producing a digital display to indicate the elapsed time in said present interval and the quantity of liquid accumulated in said container during the elapsed time in said present interval.

15. The apparatus of claim 14 wherein said measuring means includes means for producing and storing a representation of the quantity of liquid accumulated in said container during a prior interval; and wherein
    said means for producing said digital display is responsive to said representation for indicating the volume of liquid accumulated in said prior interval.

16. The apparatus of claim 15 wherein said measuring means includes electronic microprocessor means.

17. The apparatus of claim 16 wherein said container is formed by a substantially rigid wall; and wherein
    said housing includes a recess shaped to receive said container in a particular orientation with respect to said recess.

18. The apparatus of claim 13 including means for mounting said housing comprising gimbal means for orienting said housing to maintain the surface of liquid accumulated in said container substantially horizontal.

* * * * *